United States Patent [19]

Oba et al.

[11] 4,231,934
[45] Nov. 4, 1980

[54] PROCESS FOR THE PRODUCTION OF N-(HYDROXYPHENYL) MALEIMIDES

[75] Inventors: Masayuki Oba; Motoo Kawamata; Hikotada Tsuboi; Nobuhito Koga, all of Yokohama, Japan

[73] Assignee: Mitsui Toatsu Chemicals, Incorporated, Tokyo, Japan

[21] Appl. No.: 956,971

[22] Filed: Nov. 2, 1978

[30] Foreign Application Priority Data

Nov. 2, 1977 [JP] Japan .............................. 52-130905
Nov. 4, 1977 [JP] Japan .............................. 52-131504

[51] Int. Cl.³ ............................................ C07D 207/44
[52] U.S. Cl. ........................................ 260/326.5 FM
[58] Field of Search ............................ 260/326.5 FM

[56] References Cited

U.S. PATENT DOCUMENTS

| 3,265,708 | 8/1966 | Stiteler | 260/326.5 |
| 3,338,919 | 8/1967 | Nield | 260/326.44 |
| 3,758,498 | 9/1973 | Pfuller et al. | 260/326.5 FM |
| 4,130,564 | 12/1978 | Haug et al. | 260/326.5 FM |

FOREIGN PATENT DOCUMENTS 654847 10/1964 Belgium .

Primary Examiner—José Tovar

Attorney, Agent, or Firm—Fisher, Christen & Sabol

[57] ABSTRACT

N-(hydroxyphenyl) maleimides of the general formula

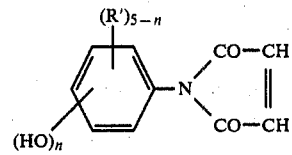

where R' stands for H, $CH_3$, $C_2H_5$, F, Cl, Br or I and n is an integer of 1–5 are produced by treating the corresponding maleamic acid or by treating the ester of said N-(hydroxyphenyl) maleimide at a temperature of 0–150° C. in the presence of at least one dehydrating agent selected from the group consisting of oxides and oxyacids of sulfur or phosphorus and alkali metal and alkaline earth metal salts of the said oxyacids. The corresponding maleamic acid can be obtained by reacting an aminophenol having one or more hydroxyl groups on its phenyl nucleus with maleic anhydride. The esters of the N-(hydroxyphenyl maleimide) can be obtained by reacting said aminophenol and said maleic anhydride in the presence of a conventional acid anhydride dehydrating agent and a conventional imide-forming cyclization catalyst.

12 Claims, No Drawings

PROCESS FOR THE PRODUCTION OF N-(HYDROXYPHENYL) MALEIMIDES

BACKGROUND OF THE INVENTION

1. Field of the Invention

This invention relates generally to a novel process for the production of N-(hydroxyphenyl) maleimides and, more particularly, to a process for producing such maleimides by dehydrative cyclization of N-(hydroxyphenyl) maleamic acids, obtained by the reaction of aminophenols with maleic anhydride, with the use of a dehydrating agent selected from oxides and oxyacids of phosphorus or sulfur, and alkali metal and alkaline earth metal salts of the oxyacids thereof, or by hydrolysis of esters of N-(hydroxyphenyl) maleimides in the presence of at least one of said dehydrating agents. The ester may be obtained by the reaction of aminophenols with maleic anhydride in the presence of a conventional imide-forming catalyst and an acid anhydride serving as a dehydrating agent.

2. Description of the Prior Art

For the production of maleimides, a process is generally known in which an amine is reacted with maleic anhydride in the presence of a catalyst such as triethylamine and sodium acetate using acetic anhydride as a dehydrating agent. Such a process, however, is not applicable when the amine is an aminophenol having one or more hydroxyl groups on its phenyl nucleus because the reaction inevitably involves esterification of the hydroxyl group due to its high reactivity, which takes place prior to the cyclic condensation reaction, resulting in the failure to yield a desired N-(hydroxyphenyl) maleimide. Further, even with the use of a catalyst generally known to be effective, such as a metal salt including sodium acetate, cobalt acetate, nickel acetate, manganese acetate, hydrates thereof and the like metal salt, and a base including triethylamine, N-dimethylbenzylamine, isoquinoline, triethylenediamine, pyridine, N-ethylmorpholine and the like base, in conjunction with an effective dehydrating agent such as an acid anhydride including propionic anhydride, butyric anhydride, benzoic anhydride and the like, the hydroxyl group is first esterified with or without subsequent cyclic condensation so that the use of such catalysts and dehydrating agents is not effective for the production of N-(hydroxyphenyl) maleimides.

To produce N-(hydroxyphenyl) maleimide derivatives, therefore, a method has been provided wherein the maleimide obtained in the abovementioned manner and, thus, containing an ester group is subjected to a transesterification or hydrolysis treatment, such as disclosed in Belgian Pat. No. 613,801 in which N-(p-hydroxyphenyl) maleimide is produced by transesterification of N-(p-acetoxyphenyl) maleimide.

However, the transesterification requires considerable time, e.g. over 14 hours. In addition, it has been revealed from extensive examination that the yield of N-(p-hydroxyphenyl)-maleimide by transesterification with methanol for 21 hours is as low as 38%, and that the reaction requires a large amount of methanol. Therefore, the conventional method is not economical on an industrial scale.

SUMMARY OF THE INVENTION

It is, accordingly, an object of the present invention to provide a process for the production of N-(hydroxyphenyl)-maleimides, which is devoid of the problems encountered in the conventional process.

The present inventors have found that high purity N-(hydroxyphenyl)-maleimide is obtained in both high yield and in short reaction times by:

(a) hydrolyzing an ester of a N-(hydroxyphenyl) maleimide in the presence of at least one dehydrating agent selected from the group consisting of oxyacids, of sulfur or phosphorus, and alkali metal salts and alkaline earth metal salts of said oxyacids under mild temperature conditions of 0°–150° C., or (b) reacting an aminophenol with maleic anhydride with or without using a solvent in the presence of a dehydrating agent selected from oxides and oxyacids of sulfur or phosphorus, alkali metal salts and alkaline earth metal salts of said oxyacids, and mixtures thereof at a temperature of 0°–150° C. and for a period of 1–10 hrs to effect a dehydrative cyclization reaction.

In accordance with the process of the present invention, there is provided a process for producing a N-(hydroxyphenyl)-maleimide expressed by the general formula:

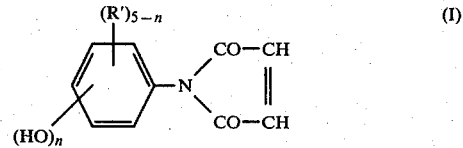

where R' stands for H, CH₃, C₂H₅, F, Cl, Br or I, and n is an integer of 1–5.

In a first aspect, this invention provides a process for producing the maleimide of formula (I), wherein an aminophenol of the general formula:

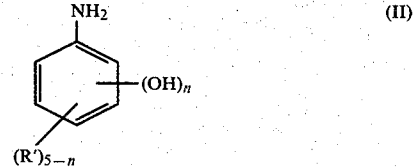

where R' and n each have the same meaning as indicated above, is reacted with maleic anhydride without using a solvent or in a polar solvent such as dimethylformamide in the presence of a dehydrating agent which is an oxide or oxyacid of sulfur or phosphorus, an alkali metal or alkaline earth metal salt of said oxyacid, or mixtures thereof at a temperature of 0°–70° C., preferably 10°–40° C. for a period of 1–5 hours to produce a N-(hydroxyphenyl) maleamic acid corresponding to the maleimide of formula I. The corresponding maleamic acid is of the general formula:

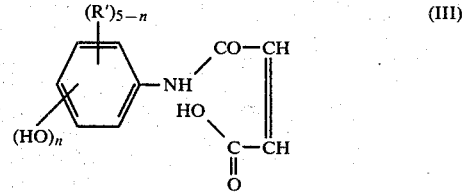

where R' and n each have the same meaning as defined above. The reaction is further continued at a temperature of 0°–150° C., preferably 50°–80° C. for a period of 1–5 hours to effect dehydrative cyclization of the maleamic acid.

In a second aspect, this invention provides a process for producing the maleimide of formula (I), in which the aminophenol of formula (II) is reacted with maleic anhydride without using a solvent or in a polar solvent such as dimethylformamide at a temperature of 0°–70° C., preferably 10°–40° C. for a time period of 1–5 hours to form the N-(hydroxyphenyl)-maleamic acid of formula (III). To the resulting reaction mixture is subsequently added a dehydrating agent which is an oxide or oxyacid of sulfur or phosphorus, an alkali metal or alkaline earth metal salt of the said oxyacid, or mixtures thereof. The dehydrating agent may be added directly to the reaction mixture or after dissolving it in the solvent. The reaction is further conducted at a temperature of 0°–150° C., preferably 50°–80° C. for a time period of 1–5 hours thereby effecting dehydrative cyclization of the maleamic acid.

In a third aspect, this invention provides a process for producing the maleimide of formula (I), wherein an ester of a N-(hydroxyphenyl) maleimide expressed by the formula:

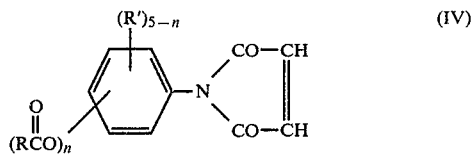

(IV)

where R' and n each has the same meaning as defined hereinabove and R stands for an alkyl group having 1 to 7 carbon atoms or a phenyl group, is subjected to hydrolysis at a temperature of 0°–150° C. in the presence of at least one of said dehydrating agents, preferably selected from the group consisting of oxyacids of sulfur or phosphorus. The ester may be obtained by reacting the aminophenol of formula (II) with maleic anhydride in the presence of a known imide-forming catalyst using an acid anhydride as a dehydrating agent.

According to the first and second aspects of the present invention, N-(hydroxyphenyl) maleimides are easily obtained in high yield without encountering any electrophilic attack to the reactive hydroxyl group while minimizing the occurrence of undesirable, tar-forming side reactions, in contrast with the conventional complicated process involving esterification and transesterification. Moreover, the N-(hydroxyphenyl) maleimides can be precipitated in crystalline form by merely adding an inactive solvent such as water to the reaction solution or by pouring the reaction solution into the inactive solvent. Thus, the separation and purification of the product are greatly facilitated in comparison with those in the conventional process.

More specifically, according to the third aspect of the invention, the ester compound of a N-(hydroxyphenyl) maleimide is first dissolved in an oxyacid of sulfur or phosphorus under relatively mild temperature conditions, e.g. 0°–150° C., and the resulting solution is then gradually added to water to effect hydrolysis and to precipitate a N-(hydroxyphenyl) maleimide in crystalline form, the crystals being separated therefrom by conventional methods. This process is characterized by effecting the hydrolysis of the ester simultaneously with the addition of the oxyacid solution of the ester to water. In the conventional process, it is necessary to conduct a hydrolysis or transesterification of the ester in the presence of a catalyst for a long time to obtain the N-(hydroxyphenyl) maleimide. In contrast, according to the third aspect of this invention, the maleimide is obtained simply by the dissolution of the ester in the oxyacid followed by the addition of the resulting solution into ice water or cold water. In addition, the yield of the maleimide product is high and the product can be easily separated and purified by any known way such as centrifuging. Accordingly, the present invention provides an extremely economical and industrially feasible process for the production of N-(hydroxyphenyl) maleimides.

The presence of one or more highly reactive hydroxyl groups as well as a double bond in the N-(hydroxyphenyl)-maleimides of the present invention provide the said imide with a variety of potential uses. For example, they can be used as raw materials for thermosetting resins obtained, e.g. by the reaction of the imide with epoxy resins, having excellent heat resistant properties and dimensional stability. They can also be used as raw materials for the production of photosensitive resins, impregnation varnishes, paints, copper clad laminates, strong adhesives and the like.

DETAILED DESCRIPTION OF THE INVENTION

In one of the embodiments of the present invention, the N-(hydroxyphenyl) maleimide is produced by the dehydrative cyclization of a N-(hydroxyphenyl) maleamic acid obtained by the reaction of an aminophenol with maleic anhydride.

The aminophenols which can be used for the process of the present invention are the compounds expressed by the formula:

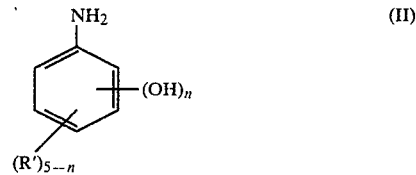

(II)

wherein R' stands for H, CH₃, C₂H₅, F, Cl, Br or I and n is an integer of 1–5. Illustrative of the aminophenols are 2-methyl-p-aminophenol, 2-chloro-p-aminophenol, p-aminophenol, m-aminophenol, o-aminophenol, 4-aminocatechol, 5-amino-2-hydroxy-p-xylene, and 3,5-dibromo-4-aminophenol.

The dehydrative cyclization of the maleamic acid is conducted in the presence of a dehydrating agent, which may be added at the maleamic acid-forming stage or at the dehydrative cyclization stage.

The dehydrating agent used in the process of the present invention is selected from oxides and oxyacids of sulfur or phosphorus, and alkali metal salts and alkaline earth metal salts of the oxyacids of sulfur and phosphorous. Illustrative of the dehydrating agents are diphosphorus trioxide, polymeric phosphorus dioxide, phosphorus pentoxide, phosphoric acid, metaphosphoric acid, pyrophosphoric acid, tripolyphosphoric acid, polyphosphoric acid, sulfur trioxide, disulfur trioxide, sulfuric acid, peroxydisulfuric acid, sodium sulfate, calcium sulfate, magnesium sulfate, sodium phosphate, etc. These compounds may be used singly or in combination. Among these, polyphosphoric acid is preferable for reasons of its strong dehydrating power, moderate chemical properties, capability of dissolving organic compounds and ease in handling. The use of sulfuric acid in conjunction with phosphorus pentoxide is also preferable because a synergistic effect is obtained due to the generation of sulfur trioxide. The dehydrating activity of the resulting mixture is superior to that attained when sulfuric acid and phosphorous pentoxide are used singly.

A variety of polar solvents may be used in the maleamic acid-forming and/or the subsequent dehydrative cyclization stages. Preferable solvents include dimethylacetoamide, dimethylformamide, dimethylsulfoxide, N-methyl-2-pyrrolidone, dioxane, dimethyl sulfone and hexamethylphosphoramide. Dimethylformamide is most preferable since it may form a chelate compound with phosphorus pentoxide or sulfur trioxide which serves to accelerate the dehydrative cyclization of the maleamic acids. The process of this invention, however, can be carried out without the abovementioned solvents when the dehydrating agent (e.g. sulfuric acid or polyphosphoric acid) also serves as a solvent.

In the process of this invention, maleic anhydride is generally used in an amount of 1–3 moles per mole of the aminophenol. However, since the N-(hydroxyphenyl) maleamic acid, the intermediate addition product, can be obtained nearly quantitatively, it is sufficient to use 1–1.3 moles of maleic anhydride per mole of the aminophenol.

The amount of the dehydrating agent used is suitably 0.1 to 10 moles per mole of the aminophenol or N-(hydroxyphenyl)-maleamic acid, whether the dehydrating agent is composed of a single component or of two or more components.

The use of the dehydrating agent is effective even in the presence of a conventional catalyst for the dehydrative cyclization of maleamic acids, e.g. sodium acetate or triethylamine.

The reaction for forming the N-(hydroxyphenyl) maleamic acid from the aminophenol and maleic anhydride is generally performed at a temperature of 0°–70° C., preferably 10°–40° C. At a temperature below 0° C., the reaction rate is low and much time is required for completing the reaction. At a temperature above 70° C., the double bond of the N-(hydroxyphenyl) maleamic acid product is thermally activated resulting in the formation of undesirable byproducts such as tarry substances.

The subsequent dehydrative cyclization of the N-(hydroxyphenyl) maleamic acid is performed generally at a temperature of 0°–150° C., preferably 50°–80° C. At temperatures below 0° C., the reaction hardly proceeds, while, at temperature over 150° C., the highly reactive dehydrating agent tends to induce a number of side reactions so that tarry substances as well as various byproducts are produced. The desired N-(hydroxyphenyl) maleimide product is considerably colored, and obtained in both lower purity and yield.

Reaction time is variable depending mainly upon the reaction temperature. Generally, the N-(hydroxyphenyl) maleamic acid-forming reaction, at 10°–40° C., is conducted for 1–5 hours and the dehydrative cyclization of the maleamic acid is at 50°–80° C. for 1–5 hours.

In another embodiment of the present invention, the N-(hydroxyphenyl) maleimide is produced by the hydrolysis of esters of N-(hydroxyphenyl) maleimides expressed by the formula:

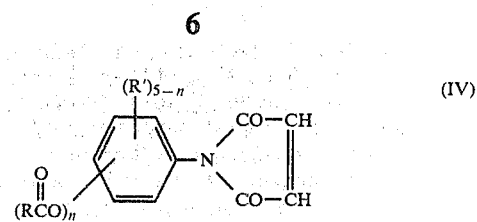

wherein R, R' and n each has the same meaning as defined hereinabove. Illustrative of the esters are N-(4-acetoxyphenyl)-maleimide, N-(2-acetoxyphenyl) maleimide, N-(4-benzoyloxyphenyl)-maleimide, N-(4-butyryloxyphenyl) maleimide, N-(4-propionyl-oxyphenyl) maleimide, N-(4-acetoxy-2,6-dibromophenyl) maleimide, N-(4-acetoxy-3,6-dimethylphenyl) maleimide and N-(3,5-diacetoxyphenyl) maleimide.

The ester of formula (IV) may be a product obtained by the dehydrative cyclization of a N-(hydroxyphenyl) maleamic acid, which has been produced by the reaction of the aminophenol expressed by the formula (II) with maleic anhydride, in the presence of both: (a) a known, effective cyclization catalyst such as sodium acetate, cobalt acetate, nickel acetate, manganese acetate, hydrates thereof, triethylamine, N-dimethyl-benzylamine, isoquinoline, triethylenediamine, pyridine and N-ethylmorpholine, and (b) an acid anhydride, such as acetic anhydride, propionic anhydride, butyric anhydride and benzoic anhydride of the formula:

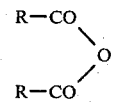

where R stands for an alkyl group having 1 to 7 carbon atoms or a phenyl group. In this case, it is not necessary to isolate the ester product from the resulting reaction mixture formed by the above conventional reaction, i.e. the resulting reaction mixture as is may be subjected to the subsequent hydrolysis according to the process of this invention to produce N-(hydroxyphenyl) maleimide.

The hydrolysis of the ester is preferably performed in the presence of at least one oxyacid of sulfur or phosphorus. Illustrative of the oxyacids are sulfuric acid, thiosulfuric acid, sulfurous acid, phosphoric acid, metaphosphoric acid and pyrophosphoric acid. These oxyacids may be used singly or in combination. When the reaction solution containing the ester product is treated with the dehydrating agent, maleamic acid which was not cyclized by the conventional cyclization catalyst and acid anhydride is cyclized by the dehydrating agent.

It is preferred that the hydrolysis be carried out in such a manner that a solution containing the ester and the oxyacid is first prepared and the solution is then added gradually to water.

Since the oxyacids of sulfur or phosphorus per se serve to act as solvents for the ester, the use of an additional solvent is unnecessary to conduct the hydrolysis. However, nonreactive solvents such as dimethylformamide, dimethylacetamide, dimethylsulfoxide and N-methyl-2-pyrrolidone may be suitably employed to enhance the dissolution of the ester.

The concentration of the ester in the solution to be added to water is within the solubility limit thereof, preferably, in the range of 80% to 90% of the solubility limit depending on the stability of the solution and the time required to completely dissolve the ester in the solvent system consisting of the oxyacid alone or the oxyacid and the above-mentioned additional solvent.

The dissolution of the ester in the solvent system is performed at a temperature of 0°–150° C., preferably 20°–80° C. Operation at a temperature below 0° C. is disadvantageous economically due to the low solubility of the ester in the solvent system. On the other hand, at a temperature above 150° C., undesirable side reactions occur between the ester and the oxyacid, resulting in the lowering in the yield of the desired product. Further, when the solution is added to water, the temperature of the water is considerably raised, sometimes to over its boiling point, due to the great heat of dilution of the solution, inducing various further side reactions. Thus, the yield of the desired N-(hydroxyphenyl) maleimide is lowered and the separation and purification of the end product become extremely difficult and troublesome.

The time required to dissolve the ester in the solvent system depends upon the type and amount of the ester, the dissolution temperature and the rate of stirring. Generally, a period of 0.5 to 5 hours is sufficient to obtain a solution with an ester concentration of 80%–90% of the solubility limit thereof.

The temperature of the water to which the ester solution is added to effect the hydrolysis, is preferably 0°–30° C. within which range the rise of the temperature of the reaction solution due to the heat of dilution is suitably suppressed. It is possible to use ice water or ice to conduct the hydrolysis.

N-(hydroxyphenyl) maleimides are partially soluble in water. In the production of such imides, it is preferred that the water contain certain salts with salting-out capabilities, such as sodium chloride, sodium sulfate and calcium chloride, in order to improve the precipitation efficiency of the product. Alternatively, the imide products dissolved in the aqueous reaction solution may be suitably recovered by extraction with ether, benzene, toluene, xylene or the like.

The following examples further illustrate the process of the invention.

EXAMPLE 1

50 g (0.216 moles) of N-(4-acetoxyphenyl) maleimide were dissolved in 100 g of sulfuric acid at 50° C. with stirring. It took 45 minutes to completely dissolve the esterified imide. The resulting solution was then gradually added to ice water which was a mixture of 200 g of ice and 100 ml of water, thereby precipitating N-(4-hydroxyphenyl) maleimide as crystals. The crystals were separated by filtration and dried to obtain 25.8 g (0.136 moles) of N-(4-hydroxyphenyl) maleimide (yield: 63.0%).

| Elementary analysis | | | | | | |
|---|---|---|---|---|---|---|
| Found | C: | 63.33 | H: | 3.80 | N: | 7.34 |
| Calculated | C: | 63.49 | H: | 3.73 | N: | 7.40 |

The results of the elementary analysis and infrared absorption spectra revealed that the acetoxy group is converted to a hydroxyl group.

EXAMPLE 2

49.0 g (0.200 moles) of N-(4-propionyloxyphenyl) maleimide were dissolved in 100 g of phosphoric acid at 60° C. It took 60 minutes to completely dissolve the esterified imide. The solution thus obtained was then added gradually to ice water of 0° C. to precipitate N-(4-hydroxyphenyl) maleimide. After filtration and drying, 22.7 g (0.120 moles) of yellowish orange crystals were obtained. The melting point of the crystals was found to be 182°–183° C. An infrared absorption spectra of the product revealed the presence of a hydroxyl group, and the product was identified as N-(4-hydroxyphenyl) maleimide.
The yield was 60.1%.

EXAMPLE 3

In a reactor, 50 ml of dimethylformamide and 21.6 g (0.22 moles) of maleic anhydride were placed, to which were gradually added 21.8 g (0.20 moles) of p-aminophenol at 20° C. with thorough stirring. After completion of the addition, the reaction was allowed to proceed at 20° C. for 2 hours to yield N-(p-hydroxyphenyl) maleamic acid. To the reaction mixture, a previously formed solution containing 70 ml of dimethylformamide, 11.4 g (0.0803 moles) of phosphorus pentoxide and 5 g (0.049 moles) of sulfuric acid, was added dropwise with the use of a dropping funnel. Thereafter, the reaction was continued at 70° C. for 2 hours. After cooling to room temperature, the resulting reaction mixture was poured into 400 ml of ice water to precipitate N-(p-hydroxyphenyl) maleimide in the form of crystals. The crystals were separated by filtration, washed with water and then dried to obtain 31.3 g (0.165 moles) of N-(p-hydroxyphenyl) maleimide (yield 82.5%).

EXAMPLE 4

Using 2-amino-5-hydroxytoluene as a starting aminophenol derivative and sulfur trioxide as a dehydrating agent, N-(2-methyl-4-hydroxyphenyl) maleimide was prepared in the same manner as in Example 3. The amount of materials used were as indicated in Table 1. The results are also shown in Table 1.

EXAMPLE 5

Using 4-aminocatechol as a starting aminophenol derivative and polyphosphoric acid and sulfuric acid as a dehydrating agent, N-(3,4-dihydroxyphenyl) maleimide was prepared in the same manner as in Example 3. The amount of materials used together with the results were as indicated in Table 1.

TABLE 1

| | Example 4 | Example 5 |
|---|---|---|
| 2-Amino-5-hydroxytoluene | 36.9 g (0.30 moles) | — |
| 4-Aminocatechol | — | 12.5 g (0.10 moles) |
| Maleic anhydride | 32.4 g (0.33 moles) | 11.7 g (0.12 moles) |
| Dimethylformamide | 80 ml | 30 ml |
| Sulfur trioxide | 52 g (0.65 moles) | — |
| Polyphosphoric acid | — | 23 g ($P_2O_3$=0.136 moles) |
| Sulfuric acid | — | 5 g (0.049 moles) |
| Maleimide produced yield | 42.1 g (69.2%) | 14.8 g (72.4%) |

EXAMPLE 6

In a reactor, 30.0 g (0.275 moles) of p-aminophenol, 29.7 g (0.303 moles) of maleic anhydride, 39.0 g (0.275 moles) of phosphorus pentoxide and 100 g of dimethylformamide were charged and stirred at 15° C. for 2 hours. The reaction mixture was then gradually heated to 60° C., at which temperature the reaction was further continued for 2.5 hours. After cooling to room temperature, the resulting reaction mixture was admixed with water to precipitate N-(p-hydroxyphenyl) maleimide in the form of crystals. The crystals were separated by filtration, washed with water and then dried to obtain 25.1 g (0.133 moles) of N-(p-hydroxyphenyl) maleimide (yield 48.2%).

EXAMPLE 7

In a reactor, 40 ml of N-methyl-2-pyrrolidone and 7.1 g (0.05 moles) of phosphorus pentoxide were charged, to which were added gradually 20.7 g (0.10 moles) of N-(m-hydroxyphenyl) maleamic acid at 20° C. with sufficient stirring. Thereafter, the reaction was continued at 70° C. for 3 hours. After cooling to room temperature, the resulting reaction mixture was admixed with water to precipitate N-(m-hydroxyphenyl) maleimide in the form of crystals. The crystals were separated by filtration, washed with water and then dried to obtain 14.8 g (0.0782 moles) of N-(m-hydroxyphenyl) maleimide (yield 78.2%).

EXAMPLE 8

In a reactor, 70 ml of dimethylformamide, 8.3 g (0.058 moles) of phosphorus pentoxide and 7.1 g (0.05 moles) of sodium sulfate were charged, to which 36.5 g (0.10 mole) of N-(3,5-dibromo-4-hydroxyphenyl) maleamic acid were gradually added at 25° C. with vigorous stirring. Thereafter, the reaction was continued at 60° C. for 3 hours. After cooling to room temperature, the resulting reaction mixture was added with water to precipitate N-(3,5-dibromo-4-hydroxyphenyl) maleimide in the form of crystals. The crystals were then separated by filtration, washed with water and dried to obtain 26.3 g (0.0757 moles) of N-(3,5-dibromo-4-hydroxyphenyl) maleimide (yield 75.7%).

EXAMPLE 9

N-(p-hydroxyphenyl) maleamic acid is obtained as in Example 3. The maleamic acid is cyclically condensed in the presence of sodium acetate and acetic anhydride to obtain a solution containing N-(4-acetoxyphenyl) maleimide. The solution is admixed with sulfuric acid at 50° C. to dissolve the esterified imide. The resulting solution is added to ice water and the precipitated crystals of N-(4-hydroxyphenyl) maleimide are separated by filtration and dried as described in Example 1.

EXAMPLE 10

The procedure of Example 9 is repeated with the exception that the N-(4-acetoxyphenyl) maleimide is isolated from the reaction solution by filtration and the isolated maleimide is admixed with the sulfuric acid.

What is claimed is:

1. A process for the production of a N-(hydroxylphenyl)-maleimide of the general formula:

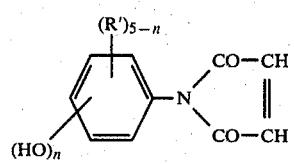

where R' stands for H, CH$_3$, C$_2$H$_5$, F, Cl, Br or I and n is an integer of 1-5, comprising treating a N-(hydroxyphenyl)-maleamic acid expressed by the general formula:

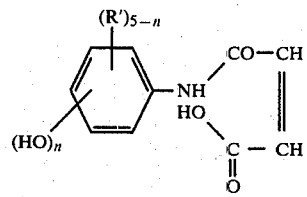

where R' and n each have the same meaning as indicated above, at a temperature of 0°-150° C. with a dehydrating agent selected from the group consisting of oxides and oxyacids of sulfur or phosphorus, alkali metal and alkaline earth metal salts of said oxyacids and mixtures thereof to effect dehydrative cyclization of the maleamic acid, said maleamic acid being obtained by the reaction of an aminophenol expressed by the general formula:

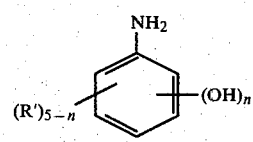

where R' and n each have the same meaning as indicated above, with maleic anhydride.

2. A process as claimed in claim 1 wherein said dehydrating agent is an oxyacid of sulfur or phosphorus.

3. A process as claimed in claim 1 wherein an inactive solvent is admixed with the reaction solution to precipitate the N-(hydroxyphenyl) maleimide.

4. A process as claimed in claim 3 wherein the inactive solvent is water.

5. A process as claimed in claim 1 wherein said aminophenol is a p-aminophenol.

6. A process as claimed in claim 1 wherein said dehydrating agent is polyphosphoric acid.

7. A process as claimed in claim 1 wherein said dehydrating agent is a mixture of sulfuric acid and phosphorus pentoxide.

8. A process as claimed in claim 1 wherein the dehydrative cyclization is performed in a polar solvent.

9. A process as claimed in claim 8 wherein said polar solvent is dimethylformamide.

10. A process as claimed in claim 1 wherein the dehydrative cyclization is performed without using a solvent.

11. A process as claimed in claim 1 wherein the aminophenol of formula III is reacted with the maleic anhydride in the presence of said dehydrating agent at a temperature of 0°-70° C. to form a mixture containing said maleamic acid of formula II, and said mixture is further treated to effect the dehydrative cyclization.

12. A process as claimed in claim 1 wherein the aminophenol of formula III is reacted with the maleic anhydride at a temperature of 0°-70° C. to form a mixture containing said maleamic acid of formula II, and said dehydrating agent is subsequently added to said mixture to effect the dehydrative cyclization.

* * * * *